United States Patent [19]

Richter et al.

[11] Patent Number: 4,638,795
[45] Date of Patent: Jan. 27, 1987

[54] MATERIAL FOR SUPPORT DRESSINGS

[75] Inventors: Roland Richter, Cologne; Hanns P. Müller, Odenthal; Christian Wegner, Cologne, all of Fed. Rep. of Germany

[73] Assignee: Bayer Aktiengesellschaft, Leverkusen, Fed. Rep. of Germany

[21] Appl. No.: 757,093

[22] Filed: Jul. 19, 1985

[30] Foreign Application Priority Data

Jul. 20, 1984 [DE] Fed. Rep. of Germany ....... 3426732

[51] Int. Cl.⁴ ............................................... A61F 5/04
[52] U.S. Cl. ..................................................... 128/90
[58] Field of Search .................... 128/90, 94; 260/77.5; 428/266, 423 X; 528/903

[56] References Cited

U.S. PATENT DOCUMENTS

| | | | |
|---|---|---|---|
| 4,052,282 | 10/1977 | Kubushiro | 128/90 |
| 4,134,397 | 1/1979 | Gianakakos | 128/90 |
| 4,376,438 | 3/1983 | Straube | 128/90 |
| 4,411,262 | 10/1983 | von Bonin | 128/90 |
| 4,570,622 | 2/1986 | von Bonin | 128/90 |

*Primary Examiner*—Gregory E. McNeill
*Attorney, Agent, or Firm*—Sprung Horn Kramer & Woods

[57] ABSTRACT

Material which hardens on access of moisture, for the production of support dressings in human medicine or veterinary medicine, which is based on a flexible carrier material impregnated and/or coated with an agent including isocyanate groups, wherein the agent contains an addition product of a sulphonyl isocyanate with a tertiary amine and/or a compound with a tin(II) or tin (IV) carboxylate structure.

10 Claims, No Drawings

MATERIAL FOR SUPPORT DRESSINGS

The present invention relates to an improved material, based on polyurethane, for support dressings for medical or veterinary use, which, in the absence of moisture, is stable to storage for a virtually unlimited period and, on entry of moisture (for example atmospheric moisture or water in liquid form) rapidly hardens to a rigid, dimensionally stable structure.

The use of bandages impregnated with gypsum as a dressing material which stiffens is known. Such gypsum dressings are undesirably heavy, have little permeability to air, rapidly lose their strength in the moist state, for example by the action of water on the hardened dressing, prevent diagnostic evaluation of X-rays because they absorb and scatter X-rays, and frequently give rise to skin irritations, caused by bacterial or fungal growth in the dressing, because of their lack of resistance to water.

There has therefore been no lack of attempts to provide dressing materials which do not have these disadvantages. Thus, for example, attempts have already been made to impregnate dressing material with polymer solutions which harden under UV light and to harden the dressing produced with these materials by irradiation with a UV Lamp (Chemical Orthopaedics and Related Research 103, 109–117 [1974]).

The use of UV emitters required here is cumbersome; furthermore, the UV light reaches only the upper layers of the dressing, so that hardening in the lower layers either does not take place at all or requires a longer time. Another serious disadvantage of this method is the fact that it is not possible to observe the fracture site by X-ray during hardening by UV irradiation.

A stiffening dressing material consisting of a flexible base material finished with substances containing hydroxycarbonylisocyanate groups is described in DT-OS (German Published Specification) No. 2,353,212. However, this dressing material of DT-OS (German Published Specification) No. 2,353,212 has not become acceptable in practice because, on the one hand, the preparation of the bandages presented difficulties which could scarcely be overcome, because of the extreme reactivity of the hydroxycarbonylisocyanates, and, on the other hand, the strength of the support dressings produced with such bandages did not fulfil requirements in practice. In addition, the high reactivity of the hydroxycarbonylisocyanates led to problems in practical application, since the substances undergo explosive decomposition on contact with water.

Support dressings, the hardening principle of which is the reaction between isocyanate groups and water molecules and which can be used in practice are described for the first time in DE-OS (German Published Specification) No. 2,357,931. The dressing materials consist of a flexible carrier material which is impregnated and/or coated with a compound containing isocyanate groups, preferably an isocyanate prepolymer. The hardening time can be varied by adding catalysts which accelerate the water/isocyanate reaction. One problem of the support dressings according to DE-OS (German Published Specification) No. 2,357,931 is that a relatively large amount of catalyst must be added in order to achieve the short hardening times desired in practice. However, these high concentrations of catalyst lead to a deterioration in the storage stability of the isocyanate prepolymers.

According to DE-OS (German Published Specification) No. 2,651,089, a substantial improvement is achieved by using a prepolymer which has aromatic NCO groups and contains a certain amount of nitrogen as the hardening component of the support dressing. The support dressings have both a satisfactory storage stability and the hardening required in practice of about 5–15 minutes.

A similar solution is described in European patent application No. A-86,621, according to which the hardening reaction of the isocyanate prepolymer is accelerated with bismorpholinodiethyl ether, that is to say a catalyst which causes little deterioration of the storage stability of the prepolymer.

According to Canadian Patent Specification No. 1,151,960, certain glass fiber fabrics are used as the flexible carrier material. The glass fibers impart such a great strength to the support dressing that substantial rigidity is already achieved in a relatively short stage of the hardening reaction with water. Only relatively little catalyst therefore has to be added to the isocyanate prepolymer, so that only little deterioration is caused in the storage stability. However, glass fiber fabrics have considerable disadvantages for support dressings, for example little X-ray transparency and the danger that the skin of the patient will be chaffed at cut surfaces by the rigid fibers.

It has now been found that the storage stability of support dresssings can be considerably improved and the hardening time can be adjusted within wide limits if an addition product of a sulphonyl isocyanate on a tertiary amine and/or on a catalyst with a tin(II) or tin(IV) carboxylate structure is introduced, as a reversibly blocked catalyst, into the compound containing isocyanate groups. Surprisingly, the catalysis of the reaction with water can thereby be adjusted so that the support dressings—in contrast to those of the abovementioned prior art—are hardened in less than 15 minutes, even by normal atmospheric moisture, and nevertheless are very stable to storage.

The invention relates to materials which can be hardened on access of moisture for the production of support dressings in human or veterinary medicine, which are based on a flexible carrier material impregnated and/or coated with a compound containing isocyanate groups, which are characterized in that the compound containing isocyanate groups contains an addition product of a sulphonyl isocyanate on a tertiary amine and/or on a compound with a tin(II) or tin(IV) carboxylate structure, as a reversibly blocked catalyst.

Possible carrier materials for the support dressings according to the invention are, besides tight or porous films or foams of natural or synthetic materials (for example polyurethanes), above all flexible sheet-like structures on a textile basis which are permeable to air, preferably with a weight per unit area of 20–1,000 g/m$^2$, in particular 30–500 g/m$^2$. Examples of suitable sheet-like structures of this type are:

1. Textile woven fabrics, knitted fabrics or mesh fabrics with a weight per unit area of 20–200 g/m$^2$, preferably 40–100 g/m$^2$, and with a thread count of preferably 2–20 threads per running centimeter in the longitudinal and transverse direction. The textile woven fabric or knitted fabric can be produced from any desired natural or synthetic yarns. However, woven fabrics or knitted fabrics which have been produced from blended yarns which have in turn been obtained both from hydrophobic threads or fibers with a high E modulus (for example polyester) and hydrophilic natural or synthetic threads or fibers (for example cotton or polyamide), are preferably employed.

2. Glass fiber woven fabrics, knitted fabrics or mesh fabrics with a weight per unit area of 60 to 500 g/m², preferably 100 to 400 g/m², and a thread count of preferably 2-20 cm in the longitudinal and transverse direction. Glass fiber woven fabrics provided with a hydrophilic size are preferred.

3. Bonded, unbonded or needled fleeces based on inorganic and preferably organic fibers with a weight per unit area of 30-400 g/m², preferably 50-200 g/m².

Fleeces with weights per unit area of up to 1,000 g/m² can also be used to produce stiffening dressings according to the invention in the form of trays or splints. Carrier materials which are suitable according to the invention are also described, for example, in U.S. patent specification No. 4,134,397, U.S. patent specification No. 3,686,725, U.S. patent specification No. 3,882,857, DE-OS (German Published Specification) No.3,211,634 and European patent application No. A-61,642.

According to the invention, possible compounds which contain isocyanate groups are all the organic polyisocyanates which are known per se, that is to say any desired compounds or mixtures of compounds which contain at least two organically bonded isocyanate groups per molecule. These include both low molecular weight polyisocyanates with a molecular weight of less than 400 and modification products of such low molecular weight polyisocyanates with a molecular weight which can be calculated from the functionality and the content of functional groups of, for example, 400 to 10,000, preferably 600 to 8,000 and in particular 800 to 5,000. Examples of suitable low molecular weight polyisocyanates are those of the formula $$Q(NCO)_n$$

in which $n=2-4$, preferably 2-3, and

Q denotes an aliphatic hydrocarbon radical with 2-18, preferably 6-10, C atoms, a cycloaliphatic hydrocarbon radical with 4-15, preferably 5-10, C atoms, an aromatic hydrocarbon radical with 6-15, preferably 6-13, C atoms or an araliphatic hydrocarbon radical with 8-15, preferably 8-13, C atoms.

Examples of suitable low molecular weight polyisocyanates of this type are hexamethylene diisocyanate, dodecane 1,12-diisocyanate, cyclobutane 1,3-diisocyanate, cyclohexane 1,3- and 1,4-diisocyanate and any desired mixtures of these isomers, 1-isocyanato-3,3,5-trimethyl-5-isocyanatomethylcyclohexane, hexahydrotoluylene 2,4- and 2,6-diisocyanate and any desired mixtures of these isomers, hexahydrophenylene 1,3- and/or 1,4-diisocyanate, perhydrodiphenylmethane 2,4'- and/or 4,4'-diisocyanate, phenylene 1,3- and 1,4-diisocyanate, toluylene 2,4- and 2,6-diisocyanate and any desired mixtures of these isomers, diphenylmethane 2,4'- and/or 4,4'-diisocyanate, naphthylene 1,5-diisocyanate, triphenylmethane 4,4'4''-triisocyanate or polyphenyl-polymethylenepolyisocyanates, such as are obtained by aniline/formaldehyde condensation and subsequent phosgenation.

Suitable higher molecular weight polyisocyanates are modification products of such simple polyisocyanates, that is to say polyisocyanates with, for example, isocyanurate, carbodiimide, allophanate, biuret or uretdione structure units, such as can be prepared by methods which are known per se from the prior art from the simple polyisocyanates of the abovementioned general formula given as examples. Of the higher molecular weight modified polyisocyanates, the prepolymers known from polyurethane chemistry which have terminal isocyanate groups and a molecular weight range of 400 to 10,000, preferably 600 to 8,000 and in particular 800 to 5,000, are particularly of interest. These compounds are prepared in a manner which is known per se by reacting excess amounts of simple polyisocyanates of the type mentioned by way of example with organic compounds with at least two groups which are reactive towards isocyanate groups, in particular organic polyhydroxy compounds. Suitable polyhydroxy compounds of this type are both simple polyhydric alcohols, such as, for example, ethylene glycol, trimethylolpropane, propane-1,2-diol or butane-1,2-diol, and, in particular, higher molecular weight polyether-polyols and/or polyester polyols of the type known per se from polyurethane chemistry with molecular weights of 600 to 8,000, preferably 800 to 4,000, and containing at least two, as a rule 2 to 8 but preferably 2 to 4, primary and/or secondary hydroxyl groups. It is of course also possible to use those NCO prepolymers which have been obtained, for example, from low molecular weight polyisocyanates of the type mentioned by way of example and less preferred compounds with groups which are reactive towards isocyanate groups, such as, for example, polythioether-polyols, polyacetals containing hydroxyl groups, polyhydroxypolycarbonates, polyesteramides containing hydroxyl groups or copolymers, containing hydroxyl groups, of olefinically unsaturated compounds. Compounds which have groups which are reactive towards isocyanate groups, in particular hydroxyl groups, and are suitable for the preparation of the NCO prepolymers are, for example, the compounds disclosed by way of example in U.S. patent specification No. 4,218,543, column 7, line 29 to column 9, line 25. In the preparation of the NCO prepolymers, these compounds with groups which are reactive towards isocyanate groups are reacted with simple polyisocyanates of the type mentioned above by way of example, an NCO-/OH equivalent ratio of $>1$ being maintained. The NCO prepolymers in general have an NCO content of 2.5 to 30, preferably 6 to 25% by weight. From this, it can already be seen that, in the context of the present invention, "NCO prepolymers" and "prepolymers with terminal isocyanate groups" are to be understood as meaning both the reaction products as such and also their mixtures with excess amounts of unreacted starting polyisocyanates, which are frequently also called "semi-prepolymers"

Polyisocyanate components which are particularly preferred according to the invention are the technical grade polyisocyanates customary in polyurethane chemistry, that is to say hexamethylene diisocyanate, 1-isocyanato-3,3,5-trimethyl-5-isocyanatomethyl-cyclohexane (isophorone diisocyanate, abbreviation: IPDI), 4,4'-diisocyanatodicyclohexylmethane, 4,4'-diisocyanatodiphenylmethane, mixtures thereof with the corresponding 2,4'- and 2,2'-isomers, polyisocyanate mixtures of the diphenylmethane series, such as can be obtained by phosgenation of aniline/formaldehyde condensates in a manner which is known per se, the modification products of these technical grade polyisocyanates containing biuret or isocyanurate groups, and, in particular, NCO prepolymers of the type mentioned based on these technical grade polyisocyanates on the one hand and the simple polyols and/or polyetherpolyols and/or polyester polyols mentioned as examples on the other hand, and any desired mixtures of such polyisocyanates. Isocyanates with aromatically bonded NCO groups are preferred according to the invention. A polyisocyanate component which is particularly preferred according to the invention is partially carbodiimidised diisocyanatodiphenylmethane, which also contains uretone-imine groups as a result of addition of monomeric diisocyanate onto the carbodiimide structure.

According to the invention, the polyisocyanates mentioned contain addition products (complexes) of sulphonyl isocyanates on any desired tertiary amines and/or on tin catalysts with tin(II) or tin(IV) structural units, as reversibly blocked catalysts.

Sulphonyl isocyanates which are suitable according to the invention are any desired inorganic or organic compounds which contain at least one structural unit of the formula

—SO$_2$—NCO

Organic sulphonyl isocyanates are preferably employed, and particularly preferably those with aromatically bonded isocyanatosulphonyl radicals. Processes for the preparation of organic sulphonyl isocyanates of the type suitable according to the invention, and their chemical properties, are summarised by H. Ulrich in Chem. Rev. 65, pages 369–376, 1965. Moreover, the preparation of arylsulphonyl isocyanates is described in U.S. patent specification No. 2,666,787 and 3,484,466. According to the invention, both aliphatic and cycloaliphatic as well as aromatic mono- or poly-sulphonyl isocyanates can be employed. Examples which may be mentioned are: methylsulphonyl isocyanate, butylsulphonyl isocyanate, cyclohexylsulphonyl isocyanate, perfluorooctylsulphonyl isocyanate, phenylsulphonyl isocyanate, p-toluenesulphonyl isocyanate, benzylsulphonyl isocyanate, p-chlorophenylsulphonyl isocyanate, m-nitrophenylsulphonyl isocyanate, 2,5-dimethylphenylsulphonyl isocyanate, p-fluorophenylsulphonyl isocyanate, 2,5-dichlorophenylsulphonyl isocyanate, 3,4-dichlorophenylsulphonyl isocyanate, p-bromophenylsulphonyl isocyanate, p-methoxyphenylsulphonyl isocyanate, p-nitrophenylsulphonyl isocyanate and o-nitrophenylsulphonyl isocyanate; m-phenylenedisulphonyl diisocyanate, p-phenylenedisulphonyl diisocyanate, 4-methyl-m-phenylenedisulphonyl diisocyanate, 2-chloro-p-phenylenedisulphonyl diisocyanate, 5-chloro-m-phenylenedisulphonyl diisocyanate, 1,5-naphthylenedisulphonyl diisocyanate, 3-nitro-p-phenylenedisulphonyl diisocyanate, 4-methoxy-m-phenylenedisulphonyl diisocyanate, 2,5-furandiylbis(-methylenesulphonyl) diisocyanate, 4,4'-bis-phenylenedisulphonyl diisocyanate, 2,2'-dichloro-4,4'-biphenylylenedisulphonyl diisocyanate, 3,3'-dimethoxy-4,4'-biphenylylenedisulphonyl diisocyanate, (methylenedi-p-phenylene)disulphonyl diisocyanate, (methylenedi-3,3'-dimethoxy-p-phenylene)disulphonyl diisocyanate, (methylenedi-3,3'-dimethyl-ophenylene)-disulphonyl diisocyanate and 2-methyl-p-phenylenedisulphonyl diisocyanate; and moreover sulphonyl isocyanates with free NCO groups, such as m-isocyanatophenylsulphonyl isocyanate, o-isocyanatophenylsulphonyl isocyanate, 3-isocyanato-p-tolylsulphonyl isocyanate, 5-isocyanato-o-tolylsulphonyl isocyanate, 3-isocyanato-4-methoxyphenylsulphonyl isocyanate, 4-isocyanato-3-chlorophenylsulphonyl isocyanate, 4'-isocyanato-4-biphenylylsulphonyl isocyanate, 4'-isocyanato-2,2'-dichloro-4-biphenylylsulphonyl isocyanate, 4'-isocyanato-3,3'-dimethoxy-4-biphenylylsulphonyl isocyanate, -α-(p-isocyanatophenyl)-p-tolylsulphonyl isocyanate, α-(4-isocyanato-3-methoxyphenyl)-2-methoxy-p-tolylsulphonyl isocyanate, α-(4-isocyanato-m-tolyl)-2,4-xylylsulphonyl isocyanate and 5-isocyanato-1-naphthylsulphonyl isocyanate; or with free isothiocyanate groups, such as p-isothiocyanatophenylsulphonyl isocyanate, m-isothiocyanatophenylsulphonyl isocyanate, 3-isothiocyanato-4-methoxyphenylsulphonyl isocyanate and 4-isothiocyanato-3-methylphenylsulph9nyl isocyanate.

Sulphonyl isocyanates in which the —SO$_2$—NCO group is bonded directly to an aromatic radical are preferably used; phenylsulphonyl isocyanate, p-chlorophenylsulphonyl isocyanate and p-toluenesulphonyl isocyanate (tosyl isocyanate) are especially preferred. It is frequently also advisable to use those sulphonyl isocyanates of the type mentioned by way of example which contain either at least two isocyanatosulphonyl structural units or, in addition to one isocyanatosulphonyl structural unit, further isocyanate groups, since, during hardening with water, such polyfunctional compounds are incorporated into the resulting polyurethane structure without a break in the chain.

According to the invention, besides the organic sulphonyl isocyanates mentioned as examples, inorganic sulphonyl isocyanates, such as, for example, chlorosulphonyl isocyanate or sulphonyl diisocyanate, the preparation of which is described, for example, in German patent specification No. 928,896 and in German patent specification No. 1,152,023, are also possible. Oxy-sulphonyl isocyanates, such as, for example, trimethylsilyloxysulphonyl isocyanate, are also suitable.

Any desired catalysts known per se from polyurethane chemistry which have either at least one tertiary amino group or at least one tin(II) or tin(IV) carboxylate structural unit are tertiary amines or tin compounds which are suitable for the preparation of the reversibly blocked catalysts. Those tertiary amines or tin carboxylates which contain no groups which are capable of reacting with isocyanate groups, in particular no hydroxyl or primary or secondary amino group, are preferably employed, since such reactive groups react with the sulphonyl isocyanate to give urethane or urea and can then form the adducts which are essential to the invention only with further sulphonyl isocyanate by reaction with the tertiary nitrogen or the carboxylate anion, and these adducts then no longer liberate the original catalyst but liberate the correspondingly derivatized product on access of water. However, since it is still entirely possible for this derivatized product to have a catalytic action, the use of catalysts which also contain free OH or aminic NH groups, in addition to a tertiary nitrogen atom or in addition to the tin carboxylate structure, although being less preferred, is not excluded. Moreover, the tertiary amines or tin compounds which are suitable according to the invention can of course contain any desired structural units which contain hetero atoms, are inert under the conditions of the hardening reaction with water and do not interfere in the use, according to the invention, of the dressing materials.

The tertiary amines which are suitable according to the invention in general have a molecular weight of between 101 and 600, preferably of 101 to 300. Examples of suitable tertiary amines are triethylamine, tributylamine, N-methyl-morpholine, N-ethyl-morpholine, N,N,N',N'-tetramethyl-ethylenediamine, pentamethyldiethylenetriamine and higher homologues (DE-OS (German Published Specification) No.2,624,527 and DE-OS (German Published Specification) No. 2,624,528), 1,4-diazabicyclo-(2,2,2)-octane, N-methyl-N'-dimethylaminoethylpiperazine, bis-(dimethylaminoalkyl)-piperazines (DE-OS (German Published Specification) No. 2,636,787), N,N-dimethylbenzylamine, N,N-dimethylcyclohexylamine, N,N-diethylbenzylamine, bis-(N,N-diethylaminoethyl) adipate, N,N,N',N'-tetramethyl-1,3-butanediamine, N,N-dimethyl-$\beta$-phenylethylamine, 1,2-dimethylimidazole, 2-methylimidazole, monocyclic and bicyclic amidines (DE-OS (German Published Specification) No. 1,720,633), bis (dialkylamino)alkyl ethers (U.S. patent specification No. 3,330,782, DE-AS (German Published Specification) No. 1,030,558, DE-OS (German Published Specification) No. 1,804,361 and DE-OS (German Published Specification) No. 2,618,280), tertiary amines containing amide groups (preferably formamide groups) according to DE-OS (German Published Specification) No. 2,523,633 and DE-OS (German Published Specification No. 2,732,292), pyridine, aminopyridines, such as 4-dimethylaminopyridine, N,N',N''-tris(dimethylaminopropyl)-s-hexahydrotriazine, N,N-diethylcyclohexylamine, N,N,N',N'-tetramethylmethanediamine, 2,2'-sulphobis(N,N-dimethylethylamine), bis[2(3'-N,N-dimethylaminopropoxy)-ethyl] ether and N-(3-dimethylaminopropyl)-morpholine. Compounds which may furthermore be mentioned are silamines with carbon-silicon bonds, such as are described, for example, in German Patent Specification No. 1,229,290, for example 2,2,4-trimethyl-2-silamorpholine and 1,3-diethylaminomethyl-tetramethyl-disiloxane. According to the invention, however, the tertiary amine nitrogen atoms can also be chemically incorporated into the polyisocyanate component. Compounds of this type are obtained, for example, by reacting polyisocyanates with alcohols containing a tertiary amine nitrogen or other compounds with reactive hydrogen, for example with dimethylethanolamine, dibutylethanolamine or the aminopolyols described in DE-OS (German Published Specification) No. 2,651,089.

Examples which may be mentioned of organic tin salts which are preferred according to the invention are: tin(II) salts of carboxylic acids, such as tin(II) acetate, tin(II) octoate, tin(II) ethylhexoate, tin(II) oleate and tin(II) laurate, and tin(IV) compounds, such as dibutyl-tin diacetate, dibutyl-tin dilaurate, dibutyl-tin maleate, dioctyl-tin diacetate, dibutyl-tin di-2-ethylhexoate, tributyl-tin acetate, 1,1,3,3-tetrabutyl-1,3-diacetoxydistannoxane or, for example, compounds of the stannosiloxane type, such as tetra-(dibutylacetoxy-stannoxy)silane.

The catalysts can be employed individually or in any desired combinations, the combination of a tin salt with a tertiary amine often being preferred, since synergism in respect of catalytic activity is frequently observed in this case.

The preparation of the addition products of the sulphonyl isocyanates on the catalysts mentioned by way of example can be effected by several variants. However, in all of these variants, the formation of the addition products of the sulphonyl isocyanates on the catalysts mentioned by way of example is preferably effected within the temperature range from 0° to 80° C., in particular 10° to 30° C., using amounts of the two components of the addition products such that at least one isocyanato-sulphonyl group of the sulphonyl isocyanates is present for each amino group of the tertiary amines or each carboxylate anion of the tin salts. The use of less than the equivalent amount of sulphonyl isocyanate is of little advantage, as can easily be seen, since only partial blocking of the catalysts would thereby be achieved.

If tertiary amines are used, the procedure is advantageously as follows:

The tertiary amine is dissolved in all of the polyisocyanate component, after which the sulphonyl isocyanate is added, with stirring. Both the tertiary amine and the sulphonyl isocyanate as well as the polyisocyanate component can be dissolved in an inert solvent here. The solvent optionally also to be used can be removed, if desired, by distillation after the reaction between the tertiary amine and sulphonyl isocyanate. The reaction mentioned can of course equally well be carried out using only some of the polyisocyanate component as the reaction medium. In such a case, the reaction mixture would be mixed with the remainder of the polyisocyanate component after the reaction (formation of the addition compound). It is of course possible for different polyisocyanates of the type mentioned above by way of example to be employed here. In a less preferred variant, it is also possible to take the sulphonyl isocyanate in the polyisocyanate component or in some of the polyisocyanate component or a solution thereof in an inert solvent and then to stir the tertiary amine into the solution thus obtained. However, the addition compounds which are essential to the invention frequently precipitate out, whereas in the preferred process variant first mentioned, the same adducts remain in solution.

In another less preferred process variant, the addition compound can be prepared, for example, in an inert solvent by combination of the individual components and the resulting solution or dispersion of the addition compound can be incorporated into the polyisocyanate component. Dispersions of the addition compounds which sediment are also frequently formed according to this less preferred process variant, but their sediments are easily redispersible by simple stirring. Stable solutions of the addition compounds in the polyisocyanate component are of course preferable to the dispersions. The surprising observation that stable solutions of this type are formed in the preferred preparation variant first mentioned may possibly be explained by the fact that isocyanate groups of the polyisocyanate component here add on to the addition compound, which is probably in the form of a betaine, in situ and thus cause the surprisingly good solubility of the addition compounds prepared in situ.

In contrast to the addition compounds based on the tertiary amines mentioned by way of example, the addition compounds based on the tin compounds mentioned by way of example have (independently of the nature of their preparation) absolute solubility in organic media and hence also in the polyisocyanate component. If organic tin compounds of the type mentioned by way of example are used, polyisocyanates in which the blocked catalyst is present in dissolved form can be obtained with equally good success by all of the variants described above.

In all the process variants, the polyisocyanate component and the individual components of the addition compound are preferably employed in amounts such that, based on the total polyisocyanate component, 0.005 to 0.3% by weight, preferably 0.05 to 0.25% by weight, of tertiary amine nitrogen or 0.008 to 8.0% by weight, preferably 0.01 to 1.0% by weight, of Sn atoms is finally present in the polyisocyanate.

The addition compounds between the tertiary amines and sulphonyl isocyanates which are essential to the invention are very probably betaines having the following structure:

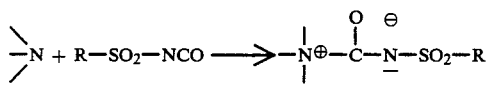

(compare DAS (German Published Specification) No.1,100,618 and Z. Brzozowski and W. Zackarewicz, Roczniki Chemii, 34, 1839 (1960)).

The structure of the addition compounds of the tin catalysts which are essential to the invention is not known, and may possibly be described by the following tautomeric formulae: Tin(II) carboxylates:

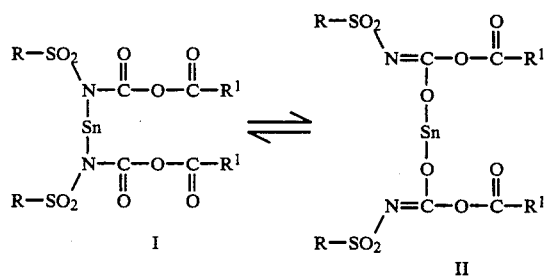

and, for example, in the case of dialkyl-tin(IV) carboxylates:

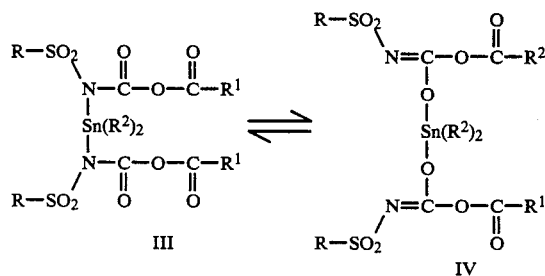

In these formulae,

R represents the inert radical of the sulphonyl isocyanate, $R^1$ represents the inert radical of the carboxylate anion and $R^2$ represents the inert organic radicals, linked directly with the tin atom in a homopolar bond, of the tin(IV) salts.

The addition compounds which are essential to the invention are 1:1 adducts of the isocyanato-sulphonyl groups on to the tertiary amino groups or the carboxylate anions. The addition compounds are extremely sensitive towards hydrolysis and are dissociated on admission of water (for example from atmospheric moisture), the catalysts being liberated. Before this hydrolytic splitting of the addition compounds which are essential to the invention, these are completely inert towards isocyanate groups and also cause no type of side reaction which impairs the storage stability of organic polyisocyanates.

The dressing materials according to the invention are produced by coating and/or impregnating the flexible carrier materials described above with preferably 50 to 300% by weight, in particular 70 to 200% by weight (based on the carrier material) of the mixture of polyisocyanate and blocked catalyst. If appropriate, the impregnating agent can be diluted here with an inert solvent (for example methylene chloride), which is stripped off again after the coating operation. Because of the extreme sensitivity of the addition compounds to be employed according to the invention towards hydrolysis, the procedure must be carried out with the complete exclusion of moisture. Any traces of moisture still present in the starting materials (for example the textile carrier) or in the air in the room can be compensated by using an excess of sulphonyl isocyanate (based on the tertiary amine nitrogen atoms or the tin compounds) for the purpose of "neutralizing" the moisture (compare U.S. patent specification No. 3,330,849 and U.S. patent specification No. 3,479,325).

The dressing materials according to the invention are preferably also prepared with the exclusion of oxygen, that is to say in a dry inert gas atmosphere (compare DE-OS (German Published Specification) No. 3,033,659). Immediately after the coating or impregnation, the dressing material is rolled up in the desired length (as a rule 2 to 5 m) on suitable spools and these are sealed in an air-tight and water-tight foil (for example polyethylene or aluminum or other completely tight containers, as is described in detail in DE-OS (German published specification) No. 2,357,931, DE-OS (German Published Specification) No. 2,651,089 and DE-OS (German Published Specification) No. 3,033,569.

Immediately before use, the material is taken out of the pack and bound around the part of the body to be supported, around which a suitable cushioning or underlining material (for example polyester fleece) has first been wound, if appropriate. The support dressing can be hardened in various ways: thus, for example, it is possible to immerse the dressing material in water immediately before application; however, it is also possible first to wind the dry dressing around the part of the body to be supported and to spray it with water; finally, as already mentioned, it is also possible to harden the dressing merely by access of atmospheric moisture. The amount of blocked catalyst is to be chosen according to the use variant, higher concentrations in the abovementioned ranges being suitable for hardening by atmospheric moisture.

Advantageously, the hardening reaction of the dressing material according to the invention does not start to proceed immediately on contact with water. Rather, initially, the catalyst is deblocked or the excess of sulphonyl isocyanate present is hydrolyzed, so that the actual crosslinking reaction between the isocyanate groups and water essentially starts up only after a certain "incubation period", which can in turn again be adjusted in a controlled manner by the concentration of catalyst or sulphonyl isocyanate with the aid of a few preliminary experiments. During this incubation period, the dressing can be applied and modelled to the part of the body of the patient.

The following examples illustrate the present invention. Unless indicated otherwise, amounts are to be understood as parts by weight or percentages by weight.

Polyisocyanate A (comparison; according to DE-OS (German Published Specification) No. 2,651,089)

100 parts of a technical grade polyphenyl-polymethylene polyisocyanate, obtained by phosgenation of an aniline/formaldehyde condensate ($\eta^{25}=200$ mPa.s; NCO content: 31%) are reacted with 32.2 parts of propoxylated triethanolamine (OH number: 150) to give a prepolymer with an NCO content of 20.2% and a viscosity $\eta^{25} = 20,000$ mPa.s. Catalyst content: 0.31% of tertiary amine nitrogen.

Polyisocyanate B (according to the invention)

200 parts of the above technical grade phosgenation product are reacted with 52 parts of polypropylene glycol (OH number: 1129 and 12.5 parts of propoxylated trimethylolpropane (OH number: 380) to give a prepolymer with an NCO content of 19.5%. Thereafter, 1.06 parts of dibutyltin dilaurate and 1.32 parts of tosyl isocyanate are stirred in, with exclusion of moisture. Even after 6 months of storage at 25° C. under exclusion of air, the viscosity of the prepolymer is virtually unchanged, whereas without the addition of tosyl isocyanate, it has solidified completely after 6 months. Catalyst content: 0.076% of Sn.

Polyisocyanate C (according to the invention)

100 parts of the above technical grade phosgenation product are reacted with 19.3 parts of propoxylated glycerol (OH number: 250) and 12.9 parts of polypropylene glcyol (OH number: 56) to give a prepolymer with an NCO content of 19.7%. Thereafter, 1.3 parts of bis-2-(dimethylamino)ethyl ether and 3.2 parts of tosyl isocyanate are stirred in, with exclusion of moisture. The storage stability of the prepolymer under exclusion of air corresponds to that under B, whereas without the addition of tosyl isocyanate, the product is already transformed into a gel state after about 2 months. Catalyst content: 0.17% of tertiary amine nitrogen.

The polyisocyanates were diluted 1:1 with $CH_2Cl_2$ and cast to a 0.2 mm thick film on glass at 22° C. and 55% relative atmospheric humidity. The hardening times (in minutes) are given in the following table:

| Polyisocyanate | Tack-free state | Dry to handle |
|---|---|---|
| A | 10 | 26 |
| B | 20 | 56 |
| C | 10 | 30 |

Dry absorbent cotton gauze bandages 2 m in length were impregnated with the above polyisocyanates (6.0 g of bandage/9.0 g of polyisocyanate), dissolved in $CH_2Cl_2$, under exclusion of water and the solvent was stripped off in vacuo. After immersion in water, the bandages were wound round a tube (diameter 4.5 cm) and left to harden. The hardening times (in minutes) are given in the following table:

| Polyisocyanate | Tack-free state | structural strength |
|---|---|---|
| A | 7 | 10–12 |
| B | 10 | 15–17 |
| C | 9 | 10–12 |

Polyisocyanate D (according to the invention)

100 parts of polyisocyanate B are additionally mixed with 1.0 part of N,N-dimethylcyclohexylamine and 4.6 parts of tosyl isocyanate. Catalyst content: 0.076% of Sn; 0.11% of tertiary amine nitrogen. The storage stability corresponds to that of B, and without tosyl isocyanate the product has solidified after 1 month.

Polyisocyanate E (according to the invention)

100 parts of polyisocyanate B are additionally stirred with 0.6 part of 1,1,3,3-tetrabutyl-1,3-diacetoxydistannoxane, $[(C_4H_9)_2(CH_3COO)_2Sn]_2O$, and 0.8 parts of tosyl isocyanate. Catalyst content: 0.31% of Sn. The storage stability corresponds to that of B; without tosyl isocyanate, the product has solidified after 2 months.

Polyisocyanates A, D and E were applied to gauze bandages by the abovementioned method as the bandages were wound and then left to harden at 22° C./55% relative atmospheric humidity. The following hardening times (in minutes) to achieve structural strength resulted:

| Polyisocyanate A: | 21–23 |
|---|---|
| D: | 24–26 |
| E: | 14–15 |

Polyisocyanate F (according to the invention)

100 parts of a technical-grade polyphenylmethylene polyisocyanate, obtained by phosgenation of an aniline/formaldehyde condensate ( 25° C.=200 mPa.s, NCO content: 31%), are reacted with 32 parts of a propoxylated trimethylolpropane (OH number: 150) to give g prepolymer having an NCO content of 20.1% and a viscosity $\eta 25°$ C.=18,000 mPa.s. Thereafter, the product is mixed with 0.82 part of trimethylsilyloxysulfonyl isocyanate and then with 1.32 parts of dibutyl-tin dilaurate. Catalyst content: 0.19% of Sn. The shelf lift is longer than two years; in the absence of the sulfonyl isocyanate, it is one month.

For comparison, polyisocyanate F and polysocyanate A were applied 4 m long gauze bandages by the method stated above (12 g of bandage/18 g of polyisocyanate) and, after appropriate immersion in water, the bandages were wound and allowed to harden. Polyisocyanate A is tack-free after 7 minutes and has bardened after 9 minutes. Polyisocyanate F is tack-free after 9 minutes and has hardened after 14 minutes.

It will be understood that the specification and examples are illustrative but not limitative of the present invention and that other embodiments within the spirit and scope of the invention will suggest themselves to those skilled in the art.

What is claimed:

1. In a material which hardens on access of moisture, for the production of support dressing in human or veterinary medicine comprising a flexible carrier material impregnated and/or coated with an agent containing isocyanate groups, the improvement wherein the agent containing isocyanate groups includes an addition product of a sulphonyl isocyanate with at least one of a tertiary amine and a compound with a tin(II) or tin(IV) carboxylate structure.

2. A material according to claim 1, wherein the agent including isocyanate groups contains 0.005 to 0.3% by weight of tertiary nitrogen atoms as the addition product.

3. A material according to claim 1, wherein the by agent including isocyanate groups contains 0.008 to 8% by weight of tin atoms as the addition product.

4. A material according to claim 2, wherein the tertiary amine nitrogen, blocked with sulphonyl isocyanate, is incorporated chemically into the agent containing isocyanate groups.

5. A material according to claim 1, wherein the agent including isocyanate groups contains the addition product in dissolved or dispersed form.

6. A material according to claim 1, wherein the agent including isocyanate groups is a prepolymer with an average molecular weight of 400 to 10,000.

7. A material according to claim 1, wherein the isocyanate groups are aromatically bonded.

8. A material according to claim 1, wherein the sulphonyl isocyanate is a compound with at least one aromatically bonded isocyanatosulphonyl group.

9. A material according to claim 1, wherein the sulphonyl isocyanate is present in excess compared with the tertiary amine nitrogen plus tin.

10. A material according to claim 1, packed in a container which is impermeable to air and moisture.

* * * * *